US008529258B2

(12) United States Patent
Doenges et al.

(10) Patent No.: US 8,529,258 B2
(45) Date of Patent: Sep. 10, 2013

(54) DENTAL IMPLEMENT FOR TOOTH RESTORATION

(75) Inventors: Scott Doenges, West Olive, MI (US); John E. Garrison, Spring Lake, MI (US); Clarke Reberg, Holland, MI (US); Kevin S. Walburg, Grand Haven, MI (US)

(73) Assignee: Garrison Dental Soultions, Spring Lake, MI (US)

( * ) Notice: Subject to any disclaimer, the term of this patent is extended or adjusted under 35 U.S.C. 154(b) by 177 days.

(21) Appl. No.: 12/070,594

(22) Filed: Feb. 20, 2008

(65) Prior Publication Data

US 2009/0208901 A1    Aug. 20, 2009

(51) Int. Cl.
*A61C 3/00*     (2006.01)
*A61C 5/04*     (2006.01)
*A61C 5/12*     (2006.01)

(52) U.S. Cl.
USPC .............................. 433/148; 433/39; 433/155

(58) Field of Classification Search
USPC ................. 433/139, 148, 149, 153, 155, 162, 433/39
See application file for complete search history.

(56) References Cited

U.S. PATENT DOCUMENTS

| | | | | |
|---|---|---|---|---|
| 388,620 | A * | 8/1888 | Booth | 433/39 |
| 427,338 | A * | 5/1890 | Marshall | 433/149 |
| 1,358,300 | A * | 11/1920 | Dailey | 433/162 |
| 1,661,068 | A * | 2/1928 | Gaillard | 433/158 |
| 5,607,302 | A | 3/1997 | Garrison et al. | |
| 6,206,697 | B1 * | 3/2001 | Hugo | 433/155 |
| 6,325,625 | B1 * | 12/2001 | Meyer | 433/139 |
| 6,336,810 | B1 | 1/2002 | Bertoletti | |
| 7,077,651 | B2 | 7/2006 | Anderson | |
| 7,284,983 | B2 * | 10/2007 | McDonald | 433/153 |
| 2002/0055084 | A1 * | 5/2002 | Fischer et al. | 433/149 |
| 2003/0059741 | A1 * | 3/2003 | Bills | 433/153 |
| 2003/0113688 | A1 * | 6/2003 | Weissenfluh | 433/149 |
| 2003/0129562 | A1 | 7/2003 | Mungcal | |
| 2004/0265779 | A1 * | 12/2004 | McDonald | 433/155 |
| 2005/0118554 | A1 * | 6/2005 | Kilcher et al. | 433/141 |
| 2007/0172793 | A1 | 7/2007 | Doenges et al. | |
| 2008/0064009 | A1 * | 3/2008 | Clark | 433/148 |

FOREIGN PATENT DOCUMENTS

EP    1 537 833 A2    6/2005

* cited by examiner

*Primary Examiner* — Todd Manahan
*Assistant Examiner* — Michael R Ballinger
(74) *Attorney, Agent, or Firm* — Watson IP Group, PLC; Jovan N. Jovanovic; Vladan M. Vasiljevic

(57) ABSTRACT

A dental implement that includes a biasing ring and a pair of opposing tines. The biasing ring includes a substantially hoop-like configuration terminating at two opposing ends which are spaced apart from each other a distance. The pair of opposing tines extend inwardly from each of the two ends of the biasing ring toward each other. Each of the pair of opposing tines is coupled to the respective opposing end about a central region thereof and extends radially outwardly therefrom. Each tine includes a front face having opposing sides, a top end and a bottom end. The front face is defined by two inwardly inclined surfaces which start at the opposing sides and incline inwardly toward each other and intersect to form a peak that extends at least partially between the top end and the bottom end of the front face. The peaks of the opposing tine assemblies face each other.

13 Claims, 8 Drawing Sheets

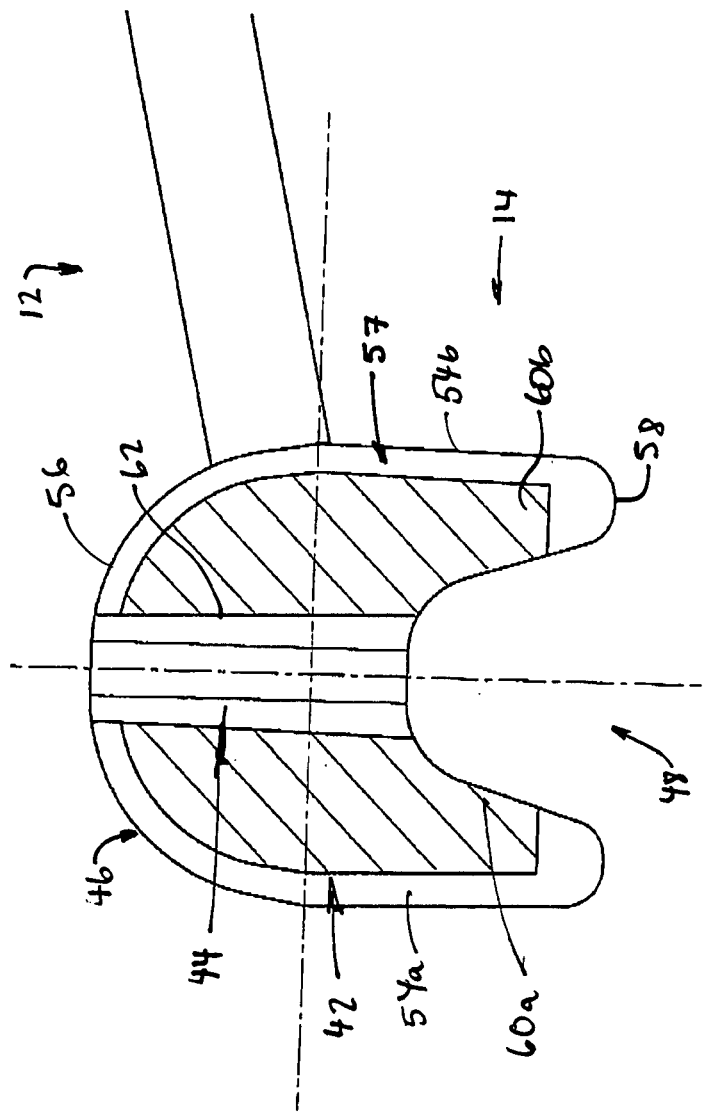

DENTAL IMPLEMENT FOR TOOTH RESTORATION

BACKGROUND OF THE DISCLOSURE

1. Field of the Disclosure

The invention relates in general to dental implements, and more particularly, to a retaining device which is used to separate teeth and to hold a matrix band in place around a tooth when a cavity in the tooth is to be filled or otherwise repaired.

2. Background Art

The use of retaining devices for holding matrix bands is well known in the art. Typically, when tooth decay occurs near the outer edges of a tooth, there is often insufficient tooth structure remaining to support the filling material prior to hardening thereof. To overcome this problem, a thin band is positioned about the tooth and secured to the tooth to provide the required support for the filling material. In such a manner, the filling material can be positioned as desired, and can be formed into the desired shape.

To achieve the proper final desired shape, it is often necessary to separate the affected tooth from the immediately adjacent teeth. This is typically accomplished through the use of open ended rings having downwardly projecting tines, the ends of which are placed on opposing sides of the region between the affected tooth and an adjacent tooth which requires separation. One such structure is shown in U.S. Pat. No. 5,607,302 issued to Garrison et al, the entire specification of which is incorporated by reference. U.S. Pub. No. 2007/0172793 A1 published to Doenges et al, the entire specification of which is incorporated by reference. Use of such a device requires the separation of the opposing tines positioned at the ends of the open ended rings, and the positioning of the respective tines on opposing sides of the teeth. When released, the spring like nature of the ring provides an inward force against the tines which drives the tines toward each other. In turn, the teeth positioned between the tines generally are forced away from each other thereby increasing the interproximal space between the two teeth.

Due to the construction of the tines, and in particular, the downward projection thereof, the tines engage the teeth but the biasing ring (and compressive force) remains above the surface of the teeth. Thus, a moment or a rotative force is created. Other designs, while utilizing downwardly projecting tines, have attempted to contact a greater portion of the tooth by replacing the downward tines with surfaces (often v-shaped surfaces). While such a tine may engage a greater portion of the surface, the downward projection of the tine nevertheless places forces against the two teeth that are less than optimal.

It is an object of the present invention to provide an improved surface contact between the tooth and the tines of the dental implement.

It is another object of the present invention to provide for an increased tooth grasping region for the tines of the dental implement by placing the biasing force more directly onto the tooth face.

It is another object of the invention to provide for an improved following of the contours of the tooth by the tines of the dental implement.

It is another object of the invention to improve the ease of placement of the dental implement by a dental professional.

It is another object of the invention to press the tines at or below the height of contour of the tooth.

These objects as well as other objects of the present invention will become apparent in light of the present specification, claims, and drawings.

SUMMARY OF THE DISCLOSURE

The disclosure is directed to a dental implement comprising a biasing ring and a pair of opposing tines. The biasing ring has a substantially hoop-like configuration terminating at two opposing ends which are spaced apart from each other a distance. The pair of opposing tines extend inwardly from each of the two ends of the biasing ring toward each other. Each of the pair of opposing tines is coupled to the respective opposing end about a central region thereof and extends radially outwardly therefrom. Each tine includes a front face having opposing sides, a top end and a bottom end. The front face is defined by two inwardly inclined surfaces which start at the opposing sides and incline inwardly toward each other and toward the opposing tine to form a peak region that extends at least partially between the top end and the bottom end of the front face. The peak regions of the opposing tine assemblies face each other.

The opposing peak regions are structurally configured for positioning proximate a interproximal space between adjacent teeth on opposing sides thereof. The inclined surfaces of each of the opposing tine assemblies are, in turn, forced against adjacent teeth on either side of a interproximal space.

In a preferred embodiment, the peak region of at least one of the tines comprises a first material and the inclined surfaces comprise a second material. The first material is harder than the second material. The second material is deformable upon biasing thereof against a tooth by the biasing ring.

In another preferred embodiment, the inclined surfaces of at least one of the tines further includes a gripping region proximate the bottom end thereof. The gripping region has a third material. The third material is harder than the second material.

In one such preferred embodiment, at least one of the tines further includes a frame member upon which the front face is mounted. The frame has a fourth material which is harder than the second material.

In one such preferred embodiment, the inclined surfaces of at least one of the tines further includes a gripping region proximate the bottom end thereof. The gripping region is integrally molded with the frame.

In a preferred embodiment, the inclined surfaces are outwardly concave, to, in turn, facilitate the following of a surface of adjacent teeth.

In yet another preferred embodiment, the peak region of at least one of the two tines comprises a substantially vertical element that is substantially parallel to the opposing sides of the respective tine.

In a preferred embodiment, at least one opposing end is coupled to the respective opposing tine substantially midway between the opposing sides thereof and substantially midway between the top and bottom ends thereof.

In another preferred embodiment, the biasing ring comprises a substantially uniform tubular member having a substantially uniform cross-sectional configuration.

In one such embodiment, the biasing ring further includes a secondary ring encapsulating at least a portion of the substantially uniform tubular member. The secondary ring spaced apart from the two opposing ends of the biasing ring.

In another such embodiment, the secondary ring further includes a base material of a first hardness and an overmolded region of a second hardness. The first hardness is substantially greater than the second hardness.

In yet another preferred embodiment, the dental implement includes a notch that extends through at least one of the opposing tines. The notch is defined by the inclined surfaces on opposing sides and the peak region thereabove.

In another embodiment, the opposing ring is substantially planar and the peak regions are substantially opposingly parallel to each other, the opposing ring and the a plane perpendicular to the peak intersections defining an angle therebetween of between 0° and 50°.

In another preferred embodiment, the opposing tines are substantially mirror images of each other. Additionally, preferably, the opposing tines comprise molded polymer members and the biasing ring comprises a metal member.

In another preferred embodiment, the tines may have a different configuration relative to each other, such that only one of the tines has the front face with two inclined surfaces and the peak region therebetween.

In another aspect, the invention comprises a dental implement having a biasing ring and a pair of opposing tines. The biasing ring has a substantially hoop-like configuration terminating at two opposing ends which are spaced apart from each other a distance. The pair of opposing tines extend inwardly from each of the two ends of the biasing ring toward each other. At least one of the opposing tines includes a front face having opposing sides, a top end and a bottom end. The front face is defined by two inwardly inclined surfaces which start at the opposing sides and incline inwardly toward each other and toward the opposing tine to form a peak region that extends at least partially between the top end and the bottom end of the front face. The peak region of at least one of the tines comprises a first material and the inclined surfaces comprise a second material. The first material is harder than the second material. The second material is deformable upon biasing thereof against a tooth by the biasing ring. The peak region of the at least one opposing tine is structurally configured for positioning proximate a interproximal space between adjacent teeth on opposing sides thereof, and the inclined surfaces of the at least one opposing tine are forced against adjacent teeth on either side of a interproximal space.

BRIEF DESCRIPTION OF THE DRAWINGS

The disclosure will now be described with reference to the drawings wherein:

FIG. 8 of the drawings is a front elevational view of another embodiment of an opposing tine of the dental implement, showing, in particular, a front face having a relatively harder material extending about the perimeter thereof, with a relatively softer material inward thereof.

DETAILED DESCRIPTION OF THE DISCLOSURE

Figure 1:
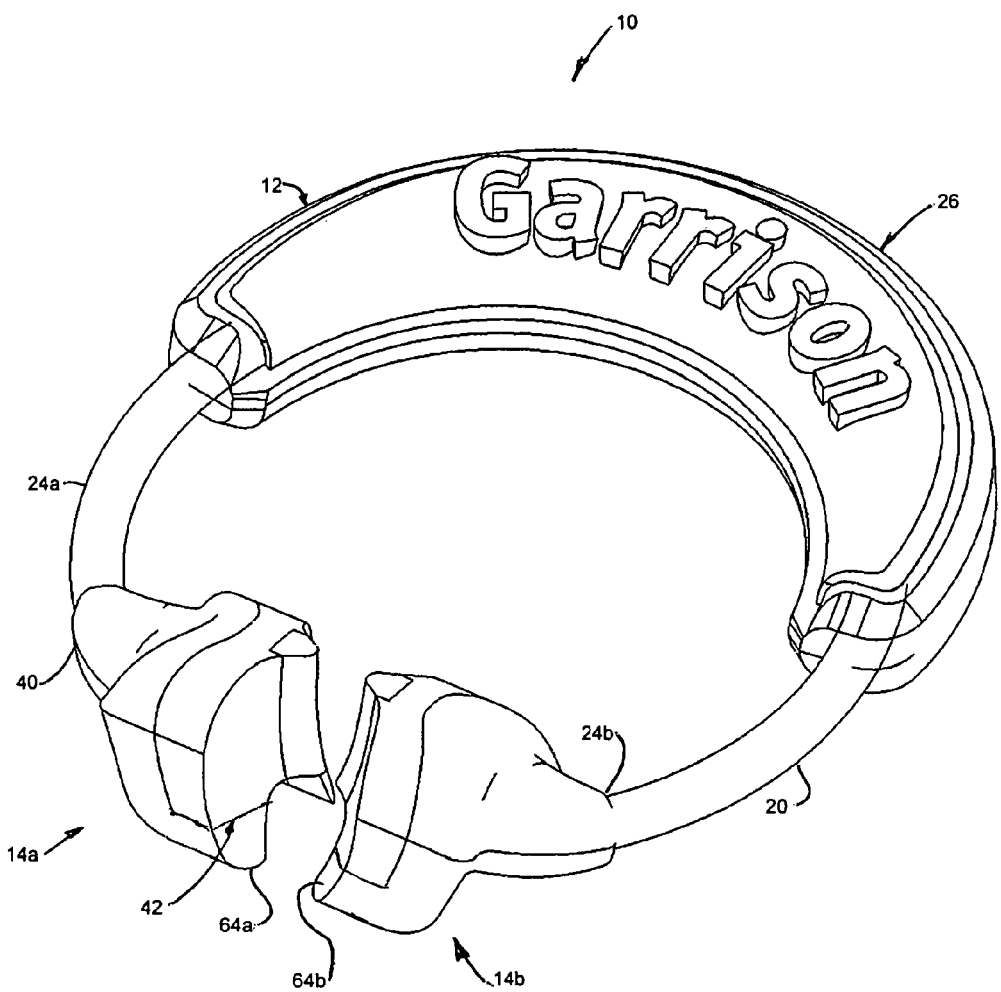
FIG. 1 of the drawings is a perspective view of the dental implement of the present invention.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the dental implement is shown generally at 10. The dental implement includes biasing ring 12 and opposing tines 14a, 14b. The dental implement is typically configured for separating adjoining teeth and for retaining a band or matrix against a tooth undergoing repair. More particularly, the opposing tines 14a, 14b press against the interproximal space between the two adjoining teeth and against the teeth themselves to provide a structure for the tooth undergoing repair. The dentist or dental practitioner can secure and shape the band with the dental implement and then fill the formed volume with a filler product.

Figure 2:
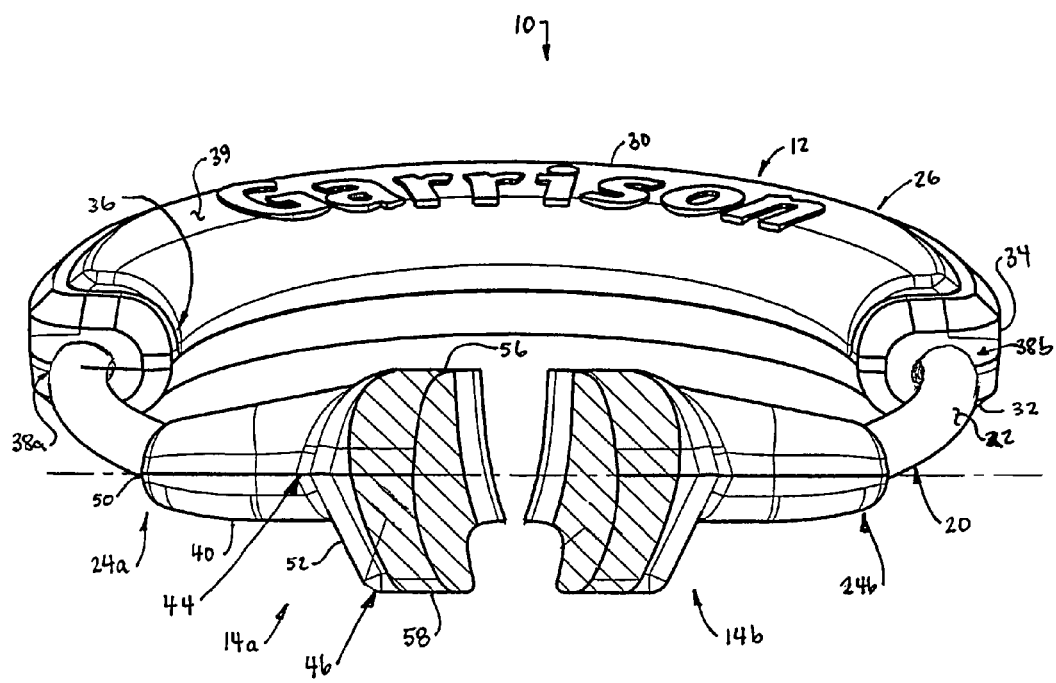
FIG. 2 of the drawings is a front elevational view of the dental implement of the present invention.
Figure 3:
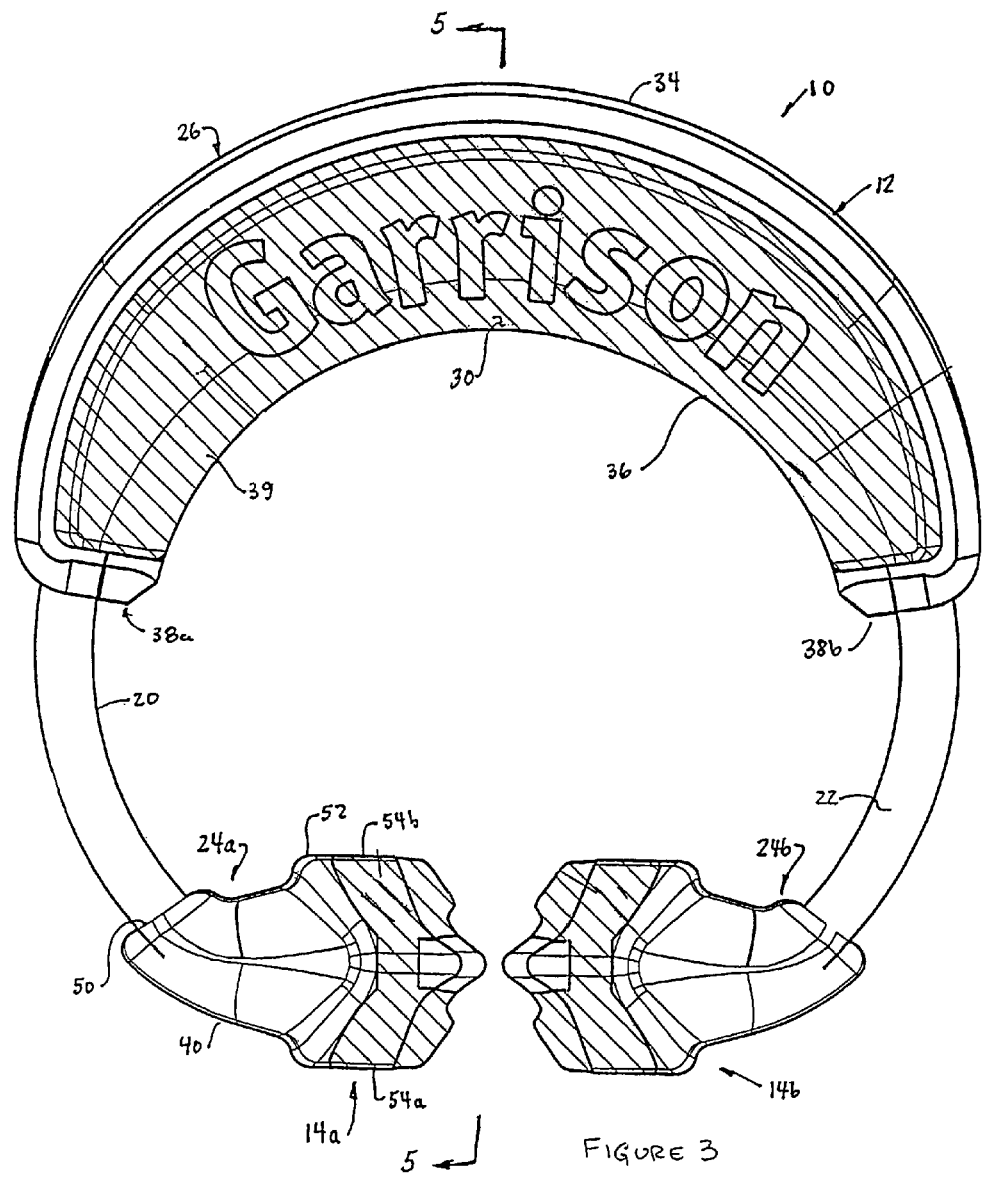
FIG. 3 of the drawings is a top plan view of the dental implement of the present invention.

With reference to FIGS. 2 and 3, the biasing ring comprises body 20 which comprises a hoop-like member having two opposing ends, a first opposing end 24a and second opposing end 24b. The two ends are configured so as to substantially face each other, separated by a distance from each other. The biasing ring additionally includes a cross-sectional configuration and an outer surface 22. The embodiment contemplated comprises a substantially circular hoop-like configuration, with a substantially circular cross-sectional configuration. In other embodiments the hoop-like configuration may comprise a square hoop-like configuration, an elliptical hoop-like configuration, a hexagonal hoop-like configuration, arbitrary hoop-like configurations. A number of hoop-like configurations are shown in FIGS. 6a through 6f. It will be understood that these hoop-like configurations are not deemed to be exhaustive, but rather are for illustrative, non-limiting purposes.

Referring again to FIGS. 2 and 3, the biasing ring further may include secondary ring 26 is molded over a portion of the biasing ring. The secondary ring includes a top surface 30, bottom surface 32, outside surface 34, inside surface 36. The secondary ring 26 comprises, preferably a rigid polymer that is molded onto the biasing ring. Polymers that are contemplated comprises a polypropylene, polyethylene and/or nylon material among others. The secondary ring extends about a portion of the hoop-like configuration terminating at first end 38a and second end 38b. In the embodiment shown, the secondary ring extends over approximately half of the hoop-like configuration. Additionally, the top and bottom surfaces are thinnest at the ends and thickest at an end opposite of the opposing ends 24a, 24b of the body. Of course, the dimensions and the relative widths and thicknesses can be varied within the scope of the invention.

The secondary ring 26 may further include an over-mold gripping region 39 which extends over a portion of the top surface 30, and inside surface 36 of the secondary ring 26. The over-mold gripping region 39 generally comprises a silicone material which is substantially softer than the surrounding rigid polymer biasing ring. Of course other relatively resilient polymers, such as elastomers or such and rubber are likewise contemplated for use.

The opposing tines 14a, 14b are shown in FIG. 1. The opposing tines 14a, 14b in the preferred embodiment are substantially mirror images of each other about a vertical plane substantially positioned between the interproximal space of the opposing tines. As a result, the opposing tine 14a will be described with the understanding that the opposing tine 14b is substantially a mirror image thereof. The same reference numbers will be utilized with respect to each of the two tines. It will be understood that the tines are molded to (or otherwise integral with the biasing ring) such that they cannot move relative to each other. In other embodiments, the tines may be able to rotate (or pivot) about an axis defined by the opposing end of the biasing ring.

With reference to FIGS. 2 and 3, the opposing tine 14a includes frame 40, and front face 42 (FIG. 1). The frame 40 comprises a molded polymer and includes bore 50 and front surface support 52. The bore is sized to receive and securely retain the opposing end 24a of the body 20 of the biasing ring 12. The front surface support 52 comprises a substantially planar member which is configured to receive the front face thereon. In one embodiment, a substantially rigid polymer is utilized to form the frame 40.

The overall tine defines a central region 44 and an outer perimeter 46 which extends radially away from the central region. The opposing end 24a is coupled to this central region away from the outer perimeter, such that the tine extends radially outward from the opposing end 24a. In such a configuration, and as will be explained, the biasing ring can apply a biasing force directly against the side surface of the tooth, rather than offset from the tooth. In turn, a more uniform force can be applied and rotative forces are reduced. This leads to an improved application of the force against the tooth, a more uniform retention of the tines in the desired orientation and an improved resulting positioning.

Figure 4:
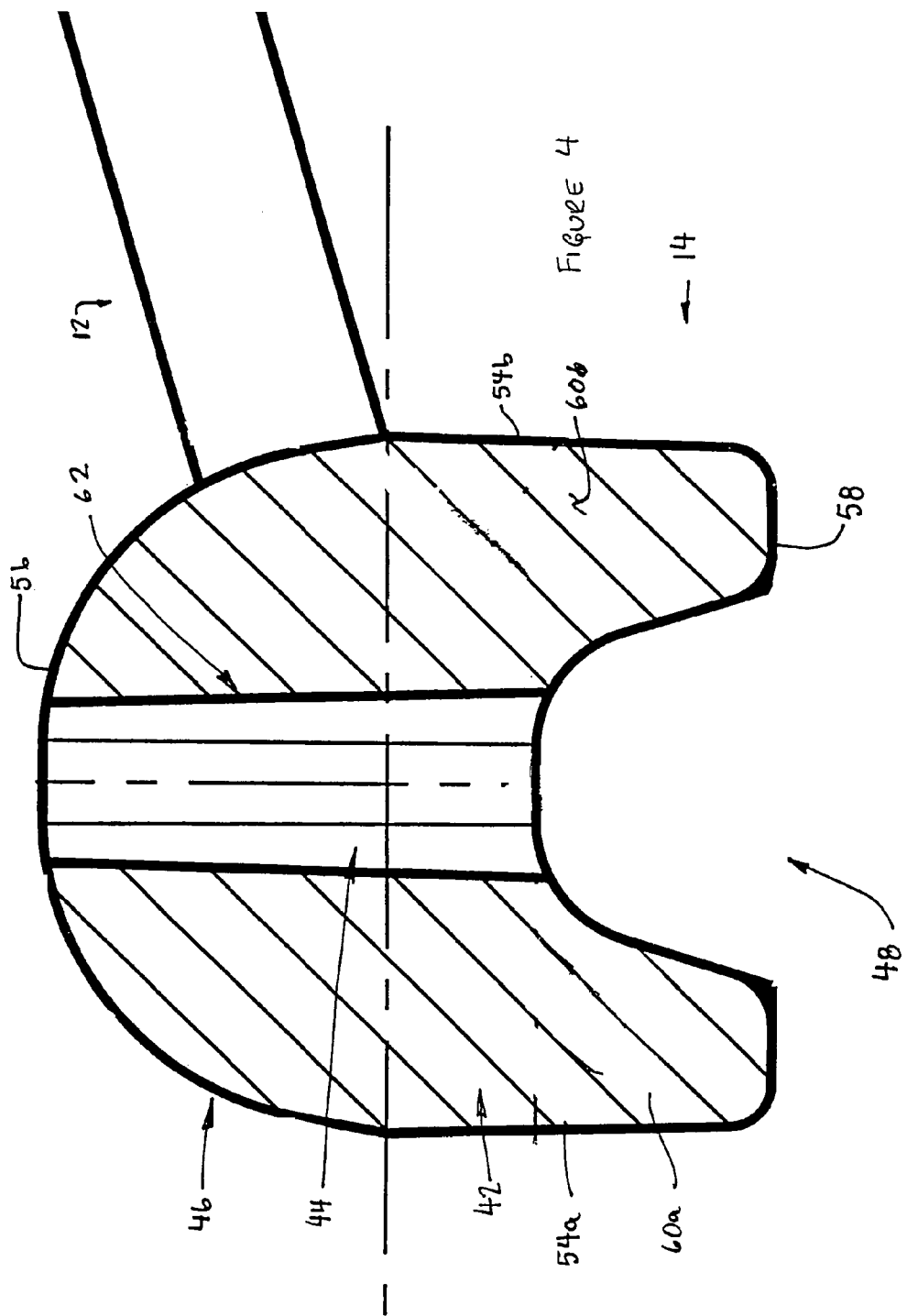
FIG. 4 of the drawings is front elevational view of an opposing tine of the dental implement of the present invention.
Figure 5:
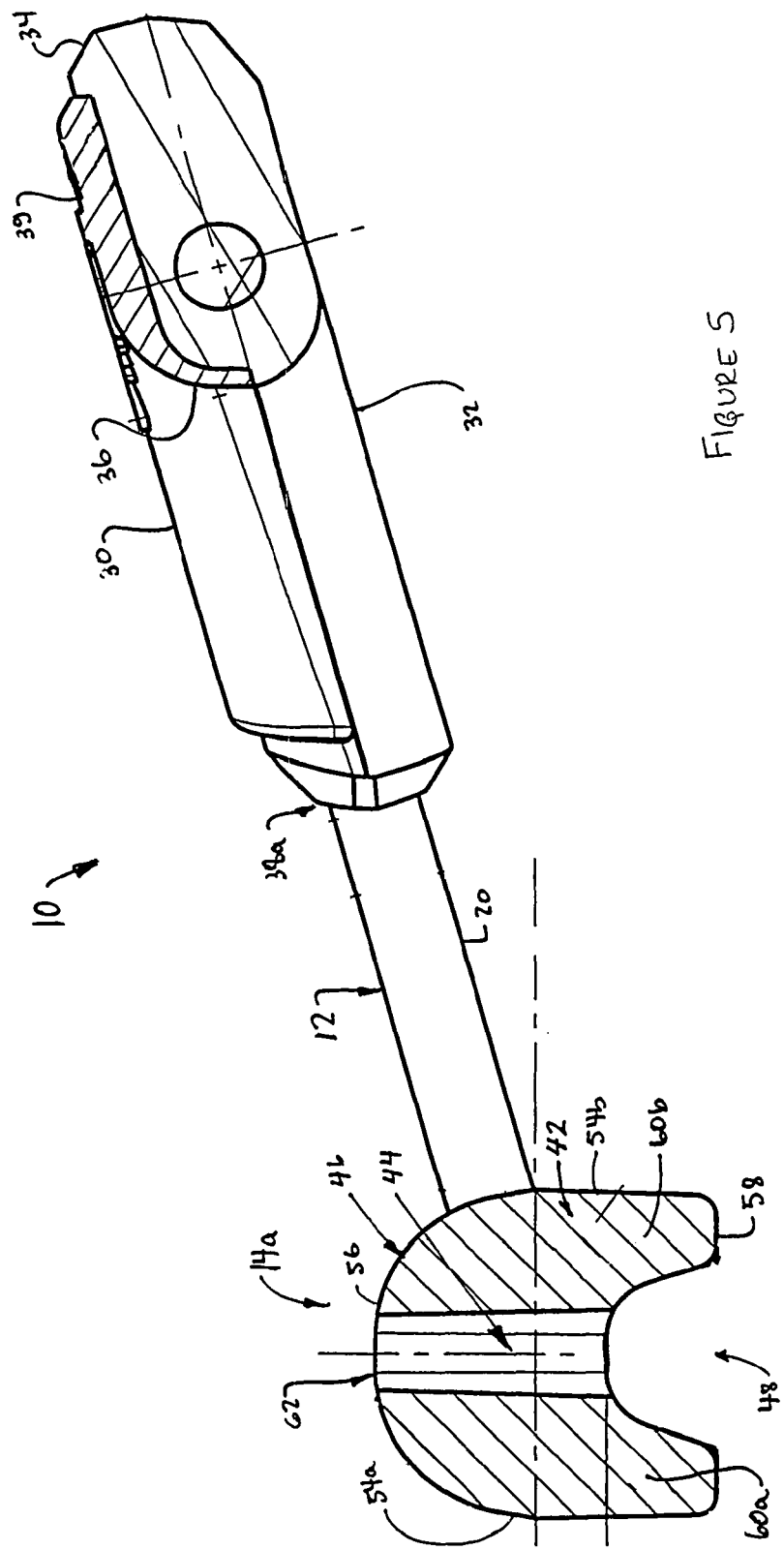
FIG. 5 of the drawings is a cross-sectional view of the dental implement taken generally about lines 5-5 of FIG. 3.
Figure 6A:
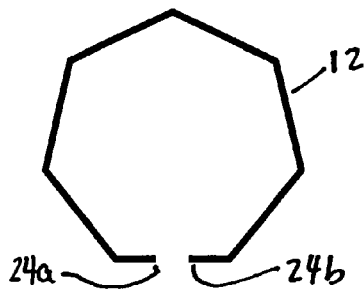
FIGS. 6a through 6f of the drawings are top plan views of the biasing ring of the dental implement of the present invention, showing in particular, illustrative examples of hoop-like configurations.
Figure 6B:
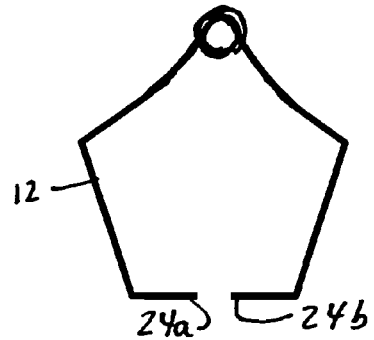
Figure 6C:
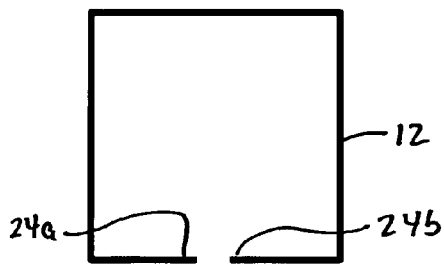
Figure 6D:
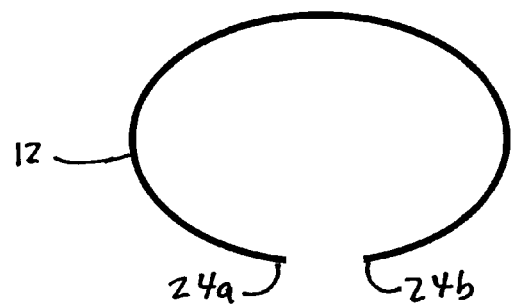
Figure 6E:
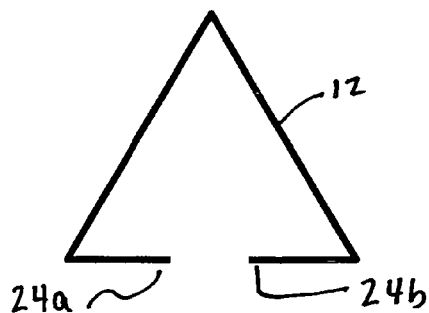
Figure 6F:
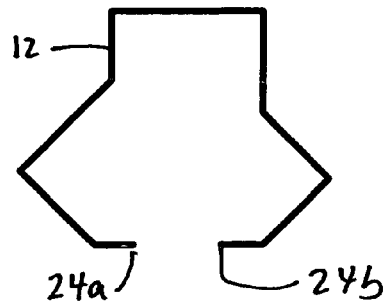

With reference to FIGS. 4 and 5, the front face is coupled to the front surface support, and in certain embodiments may be molded therewith. The front face 42 includes side edges 54a, 54b, top end 56, bottom end 58, first inclined surface 60a, second inclined surface 60b and peak region 62. The side edges and the top end of the front face are blended together through a rounded transition therebetween, such that the top end takes on an angled, almost semi-circular configuration. The bottom end is substantially perpendicular to the side edges.

The bottom end may include a notch 48 that extends through the front face and the frame in a manner which is substantially perpendicular to a plane generally defined by the outside surface of adjoining teeth. The notch is configured to receive a wedge which is commonly inserted into the interproximal space between adjoining teeth. Typically, the wedge includes a substantially triangular cross-sectional configuration, and as such, the notch comprises a substantially complementary configuration bounded by the inclined surfaces 60a, 60b and the peak region 62.

Figure 7A:
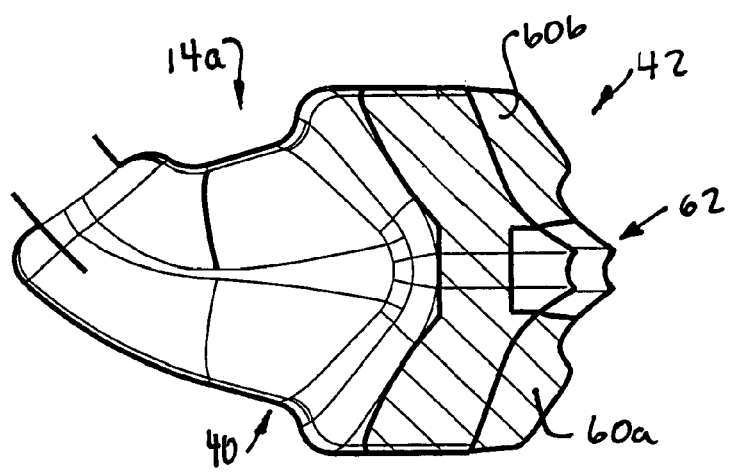
FIGS. 7a and 7b of the drawings are top plan views of various configurations of the peak region for illustrative purposes.
Figure 7B:
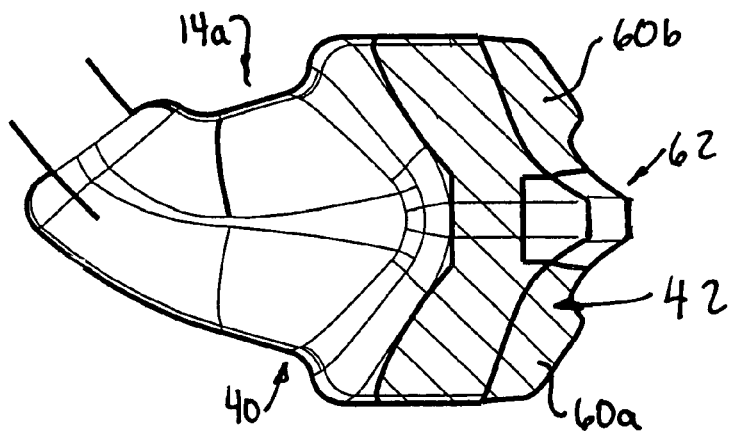

The two inclined surfaces 60a and 60b extend at an angle inwardly toward each other from the opposing side edges 54a, 54b, respectively. The inclined surfaces 60a and 60b intersect at a peak region. In the embodiment shown, the peak region comprises a substantially vertical element. Specifically, in the embodiment shown, the peak region comprises a curved line (FIGS. 2 and 3) formed by the intersection of the two surfaces. In other embodiments, an imaginary intersection of the two surfaces may exist and may be taken down so that the peak region comprises a planar surface which links the two inclined surfaces (FIG. 7b). In another embodiment, the planar surface may be replaced with an outwardly concave surface such that two spaced apart peaks can be defined with a localized valley therebetween (FIG. 7a). While a vertical element is shown, it will be understood that the verticality of the peak region may vary such that it is substantially vertical.

It is contemplated that the peak region extends from substantially midway between the side edges 54a, 54b. Additionally, it is contemplated that the peak region extends from the top end 56 to the bottom end 58 (or to notch 48). Such a configuration is, however, not required, it is possible to have the peak region spaced closer to one side edge or to the other side edge. Furthermore, the peak region can extend only partially between the top end and the bottom end (for notch 48).

As for the inclined surfaces 60a, 60b, it is contemplated that these surfaces are substantially outwardly concave. The configuration of the inclined surface is such that they substantially follow the outer configuration of a desired tooth of a human. As such, in use, the inclined surfaces have the ability to contact and follow the contours of the human teeth to which they are coupled.

The opposing tines are likewise canted such that the peak regions are closer to each other at the bottom end than at the top end, and that the respective inclined surfaces are closer to each other at the bottom end than at the top end. In this manner, the opposing inclined surfaces 60a, 60b are intended to extend below the widest point of the tooth of a user (and apply force directly thereon), thereby limiting the ability of the dental implement from popping off an installed location between two teeth.

In the preferred embodiment, the inclined surfaces comprise a material that is different from the frame member and the peak region. In particular, the peak region and the frame member may comprise substantially rigid materials (even the same material). As a result, the peak region can effectively resist deformation and press against the interproximal space between two adjoining teeth. Furthermore, the frame provides a rigid backdrop for the front face.

To the contrary, the inclined surfaces 60a, 60b generally comprise a substantially flexible and compressible polymer, such as a silicone material. This material allows for the inclined surfaces to more closely follow the contours of the tooth upon which they are biased by the biasing ring.

In the embodiment shown in FIG. 1, a portion of the front surface is formed from a material that is harder than the material from which the inclined surfaces 60a, 60b are formed. This portion is generally located at the bottom end 58 of each of the inclined surfaces on opposing sides of the notch. The region defines a gripping region 64a, 64b which tends to grip into the respective teeth at or near the gum line. In another embodiment, such as the embodiment shown in FIG. 8, the gripping region may be supplanted by a perimeter region 57 that extends substantially about the perimeter (or entirely about the perimeter) of the front face so as to encase the softer portion of the front faces. Such a construction confines the softer material of the inclined surfaces within the perimeter of the tine.

In the embodiment shown, the gripping region 64a, 64b is molded with the frame member and is of the same material as the frame member. Similarly, the peak region can be molded with the frame member, or separately. In between the frame member and the peak region, the remaining portions of the inclined surfaces 60a, 60b can be molded of a second member in a comolded process or conjointed molding process.

With reference to FIG. 5, the biasing ring is inclined relative to the tines such that the biasing ring can extend over the teeth of a user. More specifically, the biasing ring is angled at an angle of approximately 11° and 14° relative to the horizontal, wherein the peak region is substantially vertically oriented. Of course, this angle can be varied for a particular use so that the dental practitioner can insure that the biasing ring extends over the teeth and so that it does not interfere or obstruct other features or regions of the mouth. Generally, an angle of between 5° and 50° is suitable, while an angle of between 7° and 20° is preferred.

Variations to the preferred embodiment are contemplated. For example, the tines do not need to be mirror images of each other, and variations between the tines is contemplated. Furthermore, it is contemplated that rather than utilizing a metal biasing ring with a polymer secondary ring and opposing tines, the entire dental implement may comprise a molded polymer or a plurality of molded polymers. It is contemplated that a single base polymer may be utilized or a number of different polymers may be utilized. Additionally, components in excess of the biasing ring may be formed of a metal member. Furthermore, while two different hardnesses are shown for the inclined surfaces, it is contemplated that the entire inclined surfaces may comprise a single material (identical to or different from the peak region) or a number of materials in excess of two different materials. Other variations are likewise contemplated.

In operation, the user first selects an appropriately sized and shaped dental implement. It is contemplated that the dental implement may be provided in a number of sizes to correspond to a number of differently sized teeth and relative mouth dimensions. Once selected the dental practitioner or dentist (hereinafter dental professional) installs a matrix band against the tooth that is to be restored. A number of different matrix bands are available commercially, and the present invention is not limited to any particular type of matrix band or configuration of matrix band.

Once positioned, the dental professional next inserts a wedge into the interproximal space. Subsequently, the dental professional expands the biasing ring, typically with a pair of expanding jaw pliers. Specifically, the user grasps opposing sides of the ring away from the tines and engages the pliers to separate the opposing tines from each other.

Once the opposing tines have been separated to an extent that the tines can extend on opposing sides of the tooth to be restored and the adjacent tooth, the dental implement is installed into the mouth of the patient. The opposing tines are positioned so that the peak region extends into the interproximal space between two adjacent teeth, and so that the bottom end of the front face 42 is at or near the gum line. The pliers are then released, so as to gently release the opposing tines onto the adjacent teeth. As the tines make contact with the teeth, the inclined surfaces 60a, 60b of each of the tines engage the teeth. With the relatively softer material of the inclined surfaces, these surfaces will tend to compress and more closely follow the surface variations of the teeth. At the same time, the relatively rigid gripping regions 64a, 64b (in embodiments having the same) will grasp and retain the teeth at the bottom end 58 of the respective tines.

Advantageously, as the opposing rings contact the opposing tines at a central region, the force of the biasing ring is exerted directly against the front face, thereby pushing it toward and into contact with the teeth. With the shape of the inclined surfaces, the force is directed at the teeth themselves (and generally normal to the teeth), thereby limiting any twisting moment that tends to twist tines relatively to the biasing ring, or that tends to dislodge the tines from contact with the tooth. With prior art tines, the biasing ring is spaced apart from the sides of the teeth (generally resting above the tooth line), such that the force exerted by the tines on the tooth is not direct from the biasing ring, but is offset relative to the plane of the biasing ring. With the presently contemplated embodiment, the force applied by the biasing ring is direct onto the tooth. Furthermore, the biasing ring can apply pressure at or below the widest point of the tooth, directly at the tooth, further limiting the inadvertent slipping or dislodging of the dental implement from the installed location within the mouth.

Additionally, with embodiments wherein the ring is angled relative to the tines, additional dental implements may be utilized between teeth that are adjacent to the teeth to which the first dental implement is coupled. The successive biasing rings of the successive dental implements, these biasing rings appear to overlay but remain separated from each other. Thus, the dental professional can utilize multiple dental implements within a patient's mouth without interference between the separate dental implements.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A dental implement comprising:
   a biasing ring having a substantially hoop-like configuration terminating at two opposing ends which are spaced apart from each other a distance; and
   a pair of opposing tines extending inwardly from each of the two ends of the biasing ring toward each other, the at least one tine including a front face having opposing sides, a front surface support configured to receive the front face, a top end and a bottom end, the front face is defined by two inwardly inclined surfaces positioned on the front surface support which start at the opposing sides and incline inwardly toward each other and toward the opposing tine to form a peak region that is spaced apart from the opposing sides and extends substantially vertically at least partially between the top end and the bottom end of the front face,
   wherein the peak region of at least one of the tines, comprises a first material and the inclined surfaces comprise a second material positioned on the front surface support, the first material being harder than the second material, wherein the second material is deformable upon biasing thereof against a tooth by the biasing ring, and wherein the front surface support upon which the front face is positioned is harder than the second material which forms the inclined surfaces of the front face,
   wherein the peak region of the at least one opposing tine is structurally configured for positioning proximate a interproximal space between adjacent teeth on opposing sides thereof so as to contact against opposing teeth proximate the interproximal space to separate the same, and the inclined surfaces of the at least one opposing are forced against adjacent teeth on either side of a interproximal space.

2. The dental implement of claim 1 wherein the inclined surfaces are outwardly concave, to, in turn, facilitate the following of a surface of adjacent teeth.

3. The dental implement of claim 1 wherein the peak region of at least one of the two tines comprises a substantially vertical element that is substantially parallel to the opposing sides of the respective tine.

4. The dental implement of claim 1 wherein the biasing ring comprises a substantially uniform tubular member having a substantially uniform cross-sectional configuration.

5. The dental implement of claim 4 wherein the biasing ring further includes a secondary ring encapsulating at least a portion of the substantially uniform tubular member, the secondary ring spaced apart from the two opposing ends of the biasing ring.

6. The dental implement of claim 5 wherein the secondary ring further includes a base material of a first hardness and an over-molded region of a second hardness, wherein the first hardness is substantially greater than the second hardness.

7. The dental implement of claim 1 wherein the biasing ring is substantially planar and the peak regions are substantially opposingly parallel to each other, the opposing ring and a plane perpendicular to the peak intersections defining an angle therebetween of between 5° and 50°.

8. The dental implement of claim 1 wherein the opposing tines are substantially mirror images of each other.

9. The dental implement of claim 1 wherein the opposing tines comprise molded polymer members and the biasing ring comprises a metal member.

10. The dental implement of claim 1 wherein the inclined surfaces of at least one of the tines further includes a gripping region proximate the bottom end thereof, the gripping region having a third material, wherein the third material is harder than the second material.

11. The dental implement of claim 10 wherein at least one of the tines further includes a frame member upon which the front face is mounted, the frame having a fourth material, wherein the fourth material is harder than the second material.

12. The dental implement of claim 11 wherein the first, third and fourth material comprises the same material.

13. The dental implement of claim 11 wherein the inclined surfaces of at least one of the tines further includes a gripping region proximate the bottom end thereof, integrally molded with the frame.

* * * * *